(12) United States Patent
Leconte et al.

(10) Patent No.: US 7,579,506 B2
(45) Date of Patent: Aug. 25, 2009

(54) METHOD FOR THE PRODUCTION OF CYCLOHEXANONE

(75) Inventors: Philippe Leconte, Meyzieu (FR); Serge Veracini, Lyons (FR); Philippe Morel, Chuzelles (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 11/792,373

(22) PCT Filed: Nov. 30, 2005

(86) PCT No.: PCT/FR2005/002979

§ 371 (c)(1),
(2), (4) Date: Sep. 27, 2007

(87) PCT Pub. No.: WO2006/061487

PCT Pub. Date: Jun. 15, 2006

(65) Prior Publication Data

US 2008/0064902 A1 Mar. 13, 2008

(30) Foreign Application Priority Data

Dec. 7, 2004 (FR) ................................. 04 12976

(51) Int. Cl.
C07C 45/29 (2006.01)
C07C 45/53 (2006.01)
C07C 35/08 (2006.01)
(52) U.S. Cl. ...................................... 568/357; 568/836
(58) Field of Classification Search .................. 568/342, 568/836
See application file for complete search history.

(56) References Cited

U.S. PATENT DOCUMENTS 4,877,903 A * 10/1989 Costantini et al. ........... 568/342
4,918,239 A 4/1990 Wang et al.
5,168,983 A 12/1992 Tan et al.

FOREIGN PATENT DOCUMENTS

EP 0 450 498 A1 10/1991
GB 1 018 557 1/1966

OTHER PUBLICATIONS

International Search Report corresponding to PCT/FR 2005/002979, issued on Mar. 22, 2006, 4 pages.

* cited by examiner

*Primary Examiner*—Sikarl A Witherspoon
(74) *Attorney, Agent, or Firm*—Buchanan, Ingersoll & Rooney P.C.

(57) ABSTRACT

The invention relates to a method for the preparation of cyclohexanone from cyclohexane. The invention relates more particularly to a method for the production of cyclohexane whose impurity content enables cyclohexanone to be used as a raw material for the production of e-caprolactam. The inventive method consists in treating the mixture of cyclohexanol/cyclohexanone arising from oxidation of cyclohexane by oxygen in a dehydrogenation stage in order to transform cyclohexanol into cyclohexanone and the impurities present such as cyclopentenal. The inventive method makes it possible to obtain highly pure cyclohexanone which is compatible when used as a raw material in the synthesis of e-caprolactam.

14 Claims, 1 Drawing Sheet

FIG I
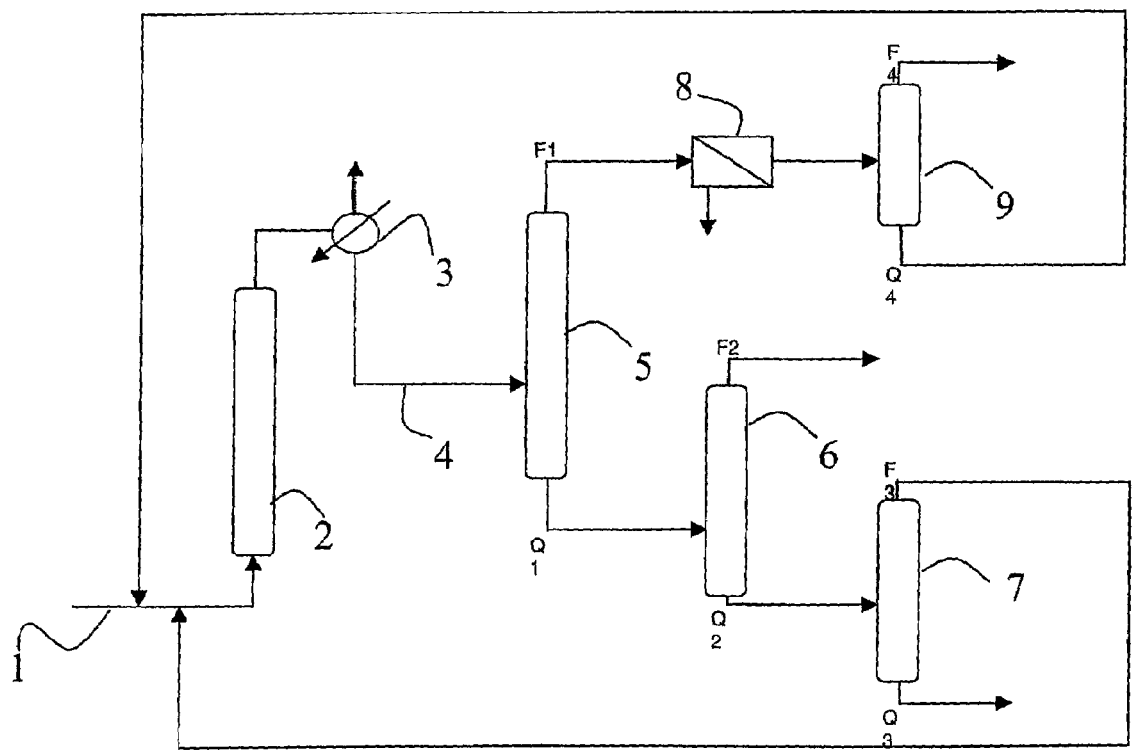

METHOD FOR THE PRODUCTION OF CYCLOHEXANONE

CROSS REFERENCE TO PRIORITY APPLICATIONS

This application is the United States national phase of International Application No. PCT/FR 2005/002979, filed Nov. 30, 2005, published in French as International Publication No. WO 2006/061487 A1 on Jun. 15, 2006, and claims priority of French Application No. 0412976, filed Dec. 7, 2004, each hereby expressly incorporated by reference in its entirety and each assigned to the assignee hereof.

The present invention relates to a method for preparing cyclohexanone from cyclohexane.

It relates more particularly to a method for preparing cyclohexanone having an impurity content that allows the use of the cyclohexanone as a raw material for producing ε-caprolactam.

The method of the invention comprises in particular a treatment of the cyclohexanol/cyclohexanone mixture produced by the oxidation by oxygen of the cyclohexane in a dehydrogenation step to convert the cyclohexanol to cyclohexanone and the impurities present such as cyclopentenal. The method of the invention is suitable for obtaining cyclohexanone with a high degree of purity, compatible with its use as a raw material for synthesizing ε-caprolactam.

The present invention relates to a method for preparing cyclohexanone from cyclohexane.

It relates more particularly to a method for preparing cyclohexanone having an impurity content that allows the use of the cyclohexanone as a raw material for producing ε-caprolactam.

In fact, nylon-6 (polyamide-6) or polycaprolactam is a major thermoplastic material for producing wires, fibres and miscellaneous moulded parts. This polymer is obtained by the polymerization of ε-caprolactam.

This compound can be obtained by various methods. One of the most widely used methods consists in producing cyclohexanone oxime from cyclohexanone.

In this method, the cyclohexanone must have a high degree of purity to avoid introducing impurities that could be disturbing, particularly in the caprolactam polymerization step, and which could also alter the properties of the polyamide obtained, particularly the coloration of the polyamide and its ageing resistance.

Cyclohexanone is generally obtained by the oxidation of liquid cyclohexane by a gas containing oxygen to produce a cyclohexanol/cyclohexanone mixture, followed, after purification and separation of the cyclohexanol from the cyclohexanone, by dehydrogenation of the cyclohexanol to cyclohexanone.

This oxidation of cyclohexane to cyclohexanone/cyclohexanol can be carried out in a single step, in the presence of an oxidation catalyst, or in a first step of oxidation of cyclohexane to cyclohexyl hydroperoxide, without catalyst, followed by catalytic decomposition of this hydroperoxide to cyclohexanol and cyclohexanone.

During these oxidation steps, many impurities are produced, such as aldehydes, acids, alcohols and ketones. It is generally impossible subsequently to convert these impurities to upgradeable products such as adipic acid and ε-caprolactam. These impurities must therefore be removed and separated from the cyclohexanone and/or cyclohexanol, particularly for producing cyclohexanone.

Methods for oxidizing cyclohexane in the presence of a catalyst comprise a step of purification of the cyclohexanone/cyclohexanol mixture by a basic treatment or distillation in basic medium. Such a basic treatment removes the impurities.

However, such a method requires supplementary treatment with the use of a new reagent, a basic compound such as a metal hydroxide. It is therefore also necessary to provide for the separation and recovery of this basic compound in the form of effluents that generally need treatment (incineration or other treatment). In the case of oxidation of cyclohexane to cyclohexyl hydroperoxide, it is also possible to implement a treatment with a basic compound, with the same advantages and drawbacks as those described above.

One of the goals of the present invention is to remedy these drawbacks by proposing a method for preparing cyclohexanone by the oxidation of cyclohexane without the need for a purification treatment using a basic compound.

For this purpose, the invention proposes a method for producing cyclohexanone characterized in that it comprises the following steps:

oxidation of cyclohexane to cyclohexyl hydroperoxide by oxygen or an oxygen-containing gas in the absence of catalyst purification of the reaction mixture by washing with water decomposition of the cyclohexyl hydroperoxide to cyclohexanol and cyclohexanone in the presence of a catalyst recovery of the cyclohexanol/cyclohexanone mixture by the separation of unreacted cyclohexane and the separation of products with higher boiling points than cyclohexanol/cyclohexanone dehydrogenation of the cyclohexanol present in the cyclohexanol/cyclohexanone mixture in the presence of a dehydrogenation catalyst distillation of the mixture obtained in a first distillation step in order to obtain a top fraction ($F_1$) comprising the compounds with lower boiling points than cyclohexanone, and a bottom fraction ($Q_1$)

distillation of the bottom fraction ($Q_1$) in a second distillation step to obtain a top fraction ($F_2$) consisting of cyclohexanone, and a bottom fraction ($Q_2$)

FIG. 1 is a schematic process flow diagram of an exemplary process for producing cyclohexanone.

The preparation of the cyclohexanol/cyclohexanone mixture as described in the first steps does not permit the removal of all the undesirable impurities, and particularly the α, β-cyclopentene-cyclopentane-1-carboxaldehyde (cyclopentenal) that is also found in the cyclohexanol/cyclohexanone mixture. This compound, which has a boiling point close to that of cyclohexanone, is very difficult to separate from it by distillation. In fact, this compound responds to certain qualification tests commonly performed to qualify cyclohexanone, particularly for synthesizing caprolactam, like the UV test carried out with a light ray at a certain wavelength or an oxidation test. In the method of the invention, this compound, cyclopentenal, is chemically converted during the dehydrogenation step to products separable from cyclohexanone by, for example, a conventional distillation operation like the one mentioned in the sequence of operations described above.

The step of dehydrogenation of the cyclohexanol present in the cyclohexanol/cyclohexanone mixture is carried out in the presence of a dehydrogenation catalyst and under the usual temperature and pressure conditions described in the literature, such as, for example, a temperature of between 200° C. and 450° C. and an absolute pressure of between 1 and 3 bar. U.S. Pat. No. 4,918,239 offers a descriptive example of this dehydrogenation step.

In one embodiment of the invention, this dehydrogenation step is carried out in the presence of a catalyst based on copper, magnesium, zinc oxides and/or mixtures thereof.

Thus, the method of the invention is suitable for producing cyclohexanone meeting the purity requirements, particularly for producing ε-caprolactam, particularly the UV test for determining the transmission of a light ray with a wavelength of 230 nm through a volume of cyclohexanone. This transmission must be higher than 86%.

According to another feature of the invention, the bottom fraction $Q_2$ is distilled in a third distillation step to obtain a top fraction ($F_3$) consisting of cyclohexanol/cyclohexanone and a bottom fraction ($Q_3$) consisting of high boiling point compounds.

The top fraction ($F_3$) is advantageously recycled into the stream of cyclohexanol/cyclohexanone mixture introduced in the cyclohexanol dehydrogenation step.

According to another feature of the method of the invention, the top fraction ($F_1$) is distilled in order to obtain a new top fraction ($F_4$) consisting of low boiling point compounds, and a new bottom fraction ($Q_4$) essentially consisting of cyclohexanone. This bottom fraction ($Q_4$) is advantageously recycled into the cyclohexanol/cyclohexanone mixture introduced in the hydrogenation step.

The method of the invention is suitable for recovering a cyclohexanone, as top fraction ($F_2$), having high purity criteria and particularly a UV test (% transmission at λ=230 nm higher than the required specification). The cyclohexanone produced by the method of the invention is therefore advantageously used for manufacturing s-caprolactam by oximation.

Other advantages and details of the invention will appear more clearly from the examples given below exclusively for information, and from the description of an embodiment of the method of the invention made with reference to the single FIGURE appended hereto, which represents a block diagram of this embodiment.

EXAMPLE 1

A mixture of cyclohexanol containing 600 ppm of cyclopentenal was fed at 1 into a column reactor 2. A catalyst was placed in a fixed bed in the column 2.

The catalyst was based on copper oxide. The temperature in the column 2 was 230° C. The degree of conversion of cyclohexanol to cyclohexanone was 30%. The cyclopentenal concentration in the reaction mixture issuing from the reactor 2 was below the limit detectable by known measurement methods, that is, less than 30 ppm.

EXAMPLE 2

A mixture containing 59% by weight of cyclohexanone, 39% by weight of cyclohexanol, 0.5% by weight of water and 1.5% by weight of heavy or light products such as impurities to be removed, is fed into the reactor 2. Particular impurities included cyclopentenal that was present in a concentration of 2950 ppm.

The feed rate of this mixture into the reactor 2 was 215 g/h. The reactor temperature was 310° C. The reaction mixture issuing from the reactor contained 80.6% by weight of cyclohexanone, 16.5% by weight of cyclohexanol, and heavy or light impurities. The cyclopentenal concentration in this medium was lower than the detection threshold, that is to say less than 30 ppm. The degree of conversion of cyclohexanol to cyclohexanone was 55%.

The reaction mixture issuing from the reactor 2 was fed into a heat exchanger 3, then via the line 4 into a first distillation column 5. This column comprised 22 theoretical stages and operated under the usual temperature and pressure conditions known to a person skilled in the art in the field of cyclohexanone distillation. The bottom fraction $Q_1$ was introduced into a second distillation column 6 also comprising 22 theoretical trays. The fraction $F_2$ recovered at the top was cyclohexanone with a degree of purity higher than 99.8% and having a transmission of 88.5% in the UV test at a wavelength of 230 nm.

In the embodiment shown, the bottom fraction $Q_2$ can be fed into a third distillation column 7 for separating the heavy products (with higher boiling point than that of cyclohexanone) in the form of a fraction $Q_3$. The top fraction $F_3$ containing cyclohexanone and cyclohexanol can be recycled into the dehydrogenation reactor 2. According to the embodiment shown in the appended FIGURE, the top fraction $F_1$ collected from the distillation column 5 can be fed into a settler 8 in order to separate the aqueous phase and then to a distillation column 9. The bottom fraction $Q_4$ collected, containing cyclohexanone, can be recycled into the reactor 2. The top fraction $F_4$ containing light products, that is to say those of low boiling points, was treated as an effluent.

EXAMPLE 3

Example 2 was repeated but by feeding into the reactor a mixture containing 59% by weight of cyclohexanone, 39% by weight of cyclohexanol, 0.5% by weight of water and 1.5% of heavy and light impurities including 360 ppm of cyclopentenal.

The feed rate of this mixture into the reactor 2 was 135 g/h. The reactor temperature was 270° C. The composition of the reaction mixture issuing from the reactor 2 was:

75.2% by weight of cyclohexanone, 22.3% by weight of cyclohexanol, and heavy or light impurities. The cyclopentenal concentration in this medium was lower than the detection threshold, that is, lower than 30 ppm. The degree of conversion of cyclohexanol to cyclohexanone was 44%. The cyclohexanone recovered as fraction $F_2$ had a cyclopentenal content of less than 30 mg/kg and a transmission of 89.5% in the UV test at 230 nm.

The invention claimed is:

1. A process for producing cyclohexanone, which consists essentially of:
   oxidizing cyclohexane to cyclohexyl hydroperoxide by oxygen in the absence of catalyst,
   purifying the resulting reaction mixture by washing with water,
   decomposing the cyclohexyl hydroperoxide to cyclohexanol and cyclohexanone in the presence of a catalyst,
   recovering the cyclohexanol/cyclohexanone mixture by the separation of unreacted cyclohexane and the separation of products with higher boiling points than cyclohexanol/cyclohexanone, wherein the cyclohexanol/cyclohexanone mixture comprises α,β-cyclopentene-cyclopentane-1-carboxaldehyde,
   dehydrogenating the cyclohexanol present in the cyclohexanol/cyclohexanone mixture in the presence of a dehydrogenation catalyst, under conditions effective to convert the α,β-cyclopentene-cyclopentane-1-carboxaldehyde to at least one compound separable from cyclohexanone by distillation,
   distilling the mixture in a first distillation step to obtain a top fraction ($F_1$) comprising the compounds with lower boiling points than cyclohexanone, and a bottom fraction ($Q_1$), and
   distilling the bottom fraction ($Q_1$), in a second distillation step to obtain a top fraction ($F_2$) comprising cyclohexanone, and a bottom fraction ($Q_2$), wherein the distillation steps are effective to separate the at least one compound separable from cyclohexanone by distillation, from the cyclohexanone.

2. The process as defined by claim 1, further consisting essentially of distilling the bottom fraction ($Q_2$) in a third distillation step to obtain a top fraction ($F_3$) which comprises cyclohexanol/cyclohexanone and a bottom fraction ($Q_3$) which comprises high boiling point compounds.

3. The process as defined by claim 2, further consisting essentially of mixing the top fraction ($F_3$) with the cyclohexanol/cyclohexanone mixture introduced in the dehydrogenation step.

4. The process as defined by claim 1, further consisting essentially of distilling the top fraction ($F_1$) in a fourth distillation step, to obtain a top fraction ($F_4$) which comprises low boiling point compounds, and a bottom fraction ($Q_4$) which comprises cyclohexanone.

5. The process as defined by claim 4, further consisting essentially of adding the bottom fraction ($Q_4$) to the cyclohexanol/cyclohexanone mixture introduced in the dehydrogenation step.

6. The process as defined by claim 1, wherein the dehydrogenation step is conducted in the presence of a catalyst selected from the group consisting of copper, magnesium and zinc oxides and mixtures thereof.

7. The process as defined by claim 1, further consisting essentially of producing ε-caprolactam from the cyclohexanone obtained in the top fraction ($F_2$).

8. A process for producing cyclohexanone, which comprises:
    oxidizing cyclohexane to cyclohexyl hydroperoxide by oxygen in the absence of catalyst,
    purifying the resulting reaction mixture by washing with water,
    decomposing the cyclohexyl hydroperoxide to cyclohexanol and cyclohexanone in the presence of a catalyst,
    recovering the cyclohexanol/cyclohexanone mixture by the separation of unreacted cyclohexane and the separation of products with higher boiling points than cyclohexanol/cyclohexanone, wherein the cyclohexanol/cyclohexanone mixture comprises α,β-cyclopentene-cyclopentane-1-carboxaldehyde,
    dehydrogenating the cyclohexanol present in the cyclohexanol/cyclohexanone mixture in the presence of a dehydrogenation catalyst, under conditions effective to convert the α,β-cyclopentene-cyclopentane-1-carboxaldehyde to at least one compound separable from cyclohexanone by distillation,
    distilling the mixture in a first distillation step to obtain a top fraction ($F_1$) comprising the compounds with lower boiling points than cyclohexanone, and a bottom fraction ($Q_1$), and
    distilling the bottom fraction ($Q_1$), in a second distillation step to obtain a top fraction ($F_2$) comprising cyclohexanone, and a bottom fraction ($Q_2$),
    wherein the distillation steps are effective to separate the at least one compound separable from cyclohexanone by distillation, from the cyclohexanone.

9. The process as defined by claim 8, further comprising distilling the bottom fraction ($Q_2$) in a third distillation step to obtain a top fraction ($F_3$) which comprises cyclohexanol/cyclohexanone and a bottom fraction ($Q_3$) which comprises high boiling point compounds.

10. The process as defined by claim 9, further comprising mixing the top fraction ($F_3$) with the cyclohexanol/cyclohexanone mixture introduced in the dehydrogenation step.

11. The process as defined by claim 8, further comprising distilling the top fraction ($F_1$) in a fourth distillation step, to obtain a top fraction ($F_4$) which comprises low boiling point compounds, and a bottom fraction ($Q_4$) which comprises cyclohexanone.

12. The process as defined by claim 11, further comprising adding the bottom fraction ($Q_4$) to the cyclohexanol/cyclohexanone mixture introduced in the dehydrogenation step.

13. The process as defined by claim 8, wherein the dehydrogenation step is conducted in the presence of a catalyst selected from the group consisting of copper, magnesium and zinc oxides and mixtures thereof.

14. The process as defined by claim 8, further comprising producing ε-caprolactam from the cyclohexanone obtained in the top fraction ($F_2$).

* * * * *